United States Patent [19]

Dellaporta

[11] Patent Number: 5,750,873
[45] Date of Patent: May 12, 1998

[54] NUCLEIC ACID MOLECULES THAT ENCODE TASSEL SEED 2(TS2), A PROTEIN INVOLVED IN THE CONTROL OF FLOWER DEVELOPMENT IN PLANTS

[75] Inventor: Stephen L. Dellaporta, New Haven, Conn.

[73] Assignee: Yale University, New Haven, Conn.

[21] Appl. No.: 440,856

[22] Filed: May 15, 1995

Related U.S. Application Data

[63] Continuation of Ser. No. 110,690, Aug. 23, 1993, abandoned.

[51] Int. Cl.$^6$ ............ A01H 5/00; C12N 15/29; C12N 15/82; C12N 15/63
[52] U.S. Cl. ............ 800/205; 536/23.1; 536/23.6; 435/69.1; 435/172.1; 435/172.3; 435/240.4; 435/240.49; 435/252.3; 435/320.1
[58] Field of Search ............ 800/205; 536/23.1, 536/23.6; 435/69.1, 172.1, 172.3, 252.3, 240.4, 240.49, 240.5, 240.51, 320.1

[56] References Cited

U.S. PATENT DOCUMENTS 4,822,949  4/1989  Niego et al. ............ 800/200

OTHER PUBLICATIONS

DeLong et al., "Cloning a Mutable Allele of the Maize tassel–seed2 Gene", Journal of Cellular Biochemistry, Supplemental 14E, issued Apr. 1990, p. 347, abstract R 507.

Oppenheimer et al., "A myb Gene Required for Leaf Trichome Differentiation in Arabidopsis Is Expressed in Stipules", Cell, 67:483–493 (1991).

Emerson, R.A., "Heritable Characters of Maize", J. Hered 11:65–76 (1920).

Hayashi et al. (1990) Cell, 63:883–894.

Lower et al. (1986) "Cucumber Breeding", In: *Breeding Vegetable Crops*, (M.J. Bassett, Co.) AVI Publ. Co., pp. 173–207.

Nickerson, N.H. et al., "Annals of the Missouri Botanical Garden", *Ann Mol Bot Gard* 42:195–212 (1955).

Phipps, I.F., "Heritable Characters in Maize", *J Hered* 19:399–404 (1928).

van der Krol et al., "An Anti–Sense Chalcone Synthase Gene in Transgenic Plants Inhibits Flower Pigmentation", Nature, 333:867–868 (1988).

*Primary Examiner*—Elizabeth McElwain
*Attorney, Agent, or Firm*—Morrison & Foerster LLP

[57] ABSTRACT

The present invention discloses the amino acid and nucleotide sequence of the TS2 protein. The present invention provides isolated nucleic acid molecules that encode the TS2 protein, vectors containing the TS2 encoding nucleic acid molecules and hosts transformed to express the TS2 protein, particularly plant hosts.

25 Claims, 12 Drawing Sheets

```
CACGCACTCG CCTCTTGTGT CTTTCTTTGT GAGCTGTGGT GTGGTGGTCG
AGACACACAC    60

AGCAGCAGCA ACAACAACAT ACATACATGC ACGCTAGCCT CGCCTCCTAC
GCCGCGGCAG   120

CTATGCCGGC GCTGGACCTC CGCCCCGAGA TAGCGCACGC GCACCAGCCC
GTCATGTCGC   180

CCTCTCACCA CGGCTGGGAC GGCAATGGCG CCACAGCCGT GCCCACACCG
ATGCCCAAGA   240

GGCTGGACGG GAAGGTGGCC ATTGTGACGG GCGGCGCGCG CGGGATCGGC
GAGGCCATCG   300

TGCGGCTGTT CGCCAAGCAC GGGGCCCGGG TGGTGATCGC GGACATCGAC
GACGCCGCGG   360

GGGAGGCGCT GGCGTCGGCG CTGGGCCCGC AGGTCAGCTT CGTGCGCTGC
GACGTGTCCG   420

TGGAGGACGA CGTCCGGCGC GCCGTGGACT GGGCGCTGTC GCGCCACGGC
GGCCGCCTCG   480

ACGTCTACTG CAACAACGCC GGGGTGCTGG CCGCCAGAC GCGCGCGGCC
AGGAGCATCC   540

TGTCCTTCGA CGCGGCCGAG TTCGACCGCG TGCTCCGCGT CAACGCGCTG
GGCGCCGCGC   600

TCGGGATGAA GCACGCCGCG CGCGCCATGG CGCCGCGCCG CGCGGGGAGC
ATCGTCTCCG   660

TCGCCAGCGT CGCGGCCGTG CTGGGCGGCC TCGGCCCGCA CGCCTACACC
GCCTCCAAGC   720
```

FIG. 3A

ACGCCATCGT CGGGCTCACC AAGAACGCCG CCTGCGAGCT GCGCGCGCAC
GGGGTCCGGG    780

TCAACTGCGT CTCGCCCTTC GGCGTCGCCA CGCCCATGCT CATCAACGCC
TGGCGCCAGG    840

GCCACGACGA CGCCACCGCC GACGCCGACC GAGACCTCGA CCTCGACCTC
GACGTCACCG    900

TGCCCAGCGA CCAGGAGGTG GAGAAGATGG AGGAGGTGGT CAGGGGCCTG
GCCACGCTCA    960

AGGGCCCCAC GCTCAGGCCC AGGGACATCG CCGAGGCGGT GCTCTTCCTG
GCCAGCGACG    1020

AGGCCAGGTA TATATCGGGC CACAACCTTG TCGTGGACGG CGGCGTCACC
ACATCCAGGA    1080

ACCTCATCGG CTTGTGAATC AATGTCAATC CGTTCCAAAT ATCCCATTCC
CATGGCTAGG    1140

CTAATTAGAG AAGGAGAGAG AGAAAACTGC TATTAGTTGT ACTTGAAGTG
ATCGATTTTC    1200

ATTTGGTTGA TTGATTCATC AAAAAAAAAA AAAAAA           1236

FIG. 3B

CTAGGACAGG GTCGTACATG CACACTACCC TCGCCTCCTA CGCCCAGGAT
CTCGCCATGC    60

CTGCCGCCGC ACTCGACCTC CTCCCTGACA AGGCGCACCA GCCGTCCATG
GCGCCGTCGC   120

TCCACGCCTG GGACTCCCCC AATGGCGCCC CCACTCCCAT GCCCAAGAGG
CTGGAAGGGA   180

AGGTGGCCAT TGTCACCGGC GGGGCGAGGG GGATCGGGGA GGCGATCGTG
AGGCTGTTCG   240

TTAAGCACGG GGCCAAGGTG GTGATCGCGG ACATCGACGA CGCGGCGGGC
GAGGCGCTGG   300

CGGCGGCGCT GGGGCCGCAC GTCGGGTTCG TGCGGTGCGA CGTGTCGGTG
GAGGAGGACG   360

TGGAGCGCGC CGTCGAGCGC GCCGTGGCGC GGTACGGGCG GCTGGACGTG
CTGTGCAACA   420

ACGCCGGGGT GCTGGGCCGC CAGACGCGCG CCGCCAAGAG CATCCTGTCG
TTCGACGCCG   480

GGGAGTTCGA CCGCGTGCTC CGCGTCAACG CGCTGGGCGC CGCGCTCGGC
ATGAAGCACG   540

CGGCGCTCGC CATGACCCAG CGCCGCGCCG GCAGCATCAT CTCCGTCGCC
AGCGTCGCCG   600

FIG. 4A

GCGTGCTCGG CGGCCTCGGC CCGCACGCCT ACACCGCCTC CAAGCACGCC
ATCGTGGGGC 660

TCACCAAGAA CGCCGCCTGC GAGCTCGGCG CCCACGGCAT CCGCGTCAAC
TGCATCTCCC 720

CCTTCGGCGT CGCCACCCCG ATGCTCATCA ACGCCTGGCG CCAGGGCCAC
GACGCCTCCA 780

CCGCCGACGA CGCCGACGCC GACATCGACC TCGACATCGC CGTGCCCAGC
GACCAGGAGG 840

TGGAGAAGAT GGAGGAGGTG GTCAGGGGCC TCGCCACGCT CAAGGGCGCG
ACGCTGAGAC 900

CCAGGGACAT CGCCGAGGCG GCGCTCTTCC TCGCCAGCGA CGACTCCAGA
TACATTTCCG 960

GCCACAACCT CGTCGTCGAC GGCGGCGTCA CCACCTCCAG AAACCTAATT
GGCCTTTGAC 1020

TCTTCTTCTC CCTCTAGATG AATGCGATAG TTTAGAACAC AACTAAAAAG
GATTTGTTAA 1080

TGTGACGCAA CGCAAGTGTA CTCAGCTTCA TCCCATTTTG TTAATCTCTT
GATTCAATGT 1140

GTTAATTGGA CTTGTGCAAC TGAGCATTGG CCCCCAAAAA AAAAAAA
1187

FIG. 4B

```
HS-TS2cDNA  CACGCACTCG CCTCTTGTGT CTTTCTTTGT GAGCTGTGGT GTGGTGGTCG   50
8(23)RICE   ---------- ---------- ---------- ---------- ----------   50
Consensus   CACGCACTCG CCTCTTGTGT CTTTCTTTGT GAGCTGTGGT GTGGTGGTCG   50

HS-TS2cDNA  AGACACACAC AGCAGCAGCA ACACAACA- -TACATACAT GCACGCTAGC   98
8(23)RICE   ---------- ---------- CACGGACAG GGTCCTACAT GCACACTACC   29
Consensus   AGACACACAC AGCAGCAGCA ACACSAACAG GKNCATACAT GCACRCTABC  100

HS-TS2cDNA  CTCGCCTCCT ACGCCGCGG-  --CAGCTATG CC-GGCGCTG GACCTCCGCC  144
8(23)RICE   CTCGCCTCCT ACGCCCAGGA TCTGCCTATG CCGGCCGCCG CA-CTCGACC   78
Consensus   CTCGCCTCCT ACGCCSMGGA TCYMGCTATG CCNGCCGCNG NACCTCBRCC  150

HS-TS2cDNA  CCGAGATAGC GCACGCGCAC CAGCCCGTCA TGCCGCCCTC TGACCACGGC  194
8(23)RICE   TCCTCCCTGA CAAGGCGCAC CAGCCGTCCA TGCCGCCCTC GACCCACGGC  128
Consensus   YCSWSMYWGM SMASGCGCAC CAGCCSKYCA TGCCGCCSTC NACCACGSC   200

H2-TS2cDNA  TGGGACGGCA ATGGCGCCAC AGCCGTGCCC ACCCGATGC CCAAGAGGCT   244
8(23)RICE   TGGGAC---- -T-CGCCCAA TGCGCCCCC ACCCATGC CCAAGAGGCT   172
Consensus   TGGGACGGCA ATGSCGCCAN WGCCGYSCCC ACCCBATGC CCAAGAGGCT   250

H2-TS2cDNA  GGACGGGAAG GTGGCCATTG TGACGGCGG CGCGCCGGG ATCGGCGAGG   294
8(23)RICE   GGAAGGGAAG GTGGCCATTG TGCCGGCGG GCCCGCGGG ATCGGGGAGG   222
Consensus   GGAMGGGAAG GTGGCCATTG TGNCGGCGG SCCSGCGGG ATCGGSGAGG   300

H2-TS2cDNA  CGATCGTGCG GCTGTTCGCC AAGCACGGGG CCCGGGTGGT GATCGCGGAC  344
8(23)RICE   CGATCGTGAG GCTGTTCGTT AAGCACGGGG CCAAGGTGGT GATCGCGGAC  272
Consensus   CSATCGTGMG GCTGTTCGYY AAGCACGGGG CCMRGGTGGT GATCGCGGAC  350

H2-TS2cDNA  ATCGACGACG CGGCGGGCGA GGCGCTGGCG TCGGCGCTGG GCCGCAGGT   394
8(23)RICE   ATCGACGACG CGGCGGGCGA GGCGCTGGCG GCGGCGCTGG GCCGCACGT   322
Consensus   ATCGACGACG CSGCGGGSGA GGCGCTGGCG NCGGCGCTGG GBCCGCANGT   400

HS-TS2cDNA  CAGCTTCGTG CGCTGCGACG TGTCCGTGGA GGACGACGTC CGGCGCGCCG  444
8(23)RICE   CGGGTTCGTG CGGTGCGACG TGTCGGTGGA GGAAGACGTG GAGCGCGCCG  372
Consensus   CRGSTTCGTG CGSTGCGACG TGTCSGTGGA GGANGACGTS SNGCGCGCCG  450

H2-TS2cDNA  TGGACTGGGC GCTGTCGCGC CACGGCGGCC GCCTCGACGT CTACTGCAAC  494
8(23)RICE   TGGA---GGC GCCGTGGCGC GGT-ACGGCC GCCTCGACGT GCTGTGCAAC  419
Consensus   TSGACTGSGC GCYGTSGCGC BRYGRCGGSC GCCTCGACGT SYWSTGCAAC  500

H2-TS2cDNA  AACGCCGGGG TGCTGGGCCG CCAGACGCGC GCGGCCAGGA GCATCCTGTC  544
8(23)RICE   AACGCCGGGG TGCTGGGCCG CCAGACGCGC GCGGCCAAGA GCATCCTGTC  469
Consensus   AACGCCGGGG TGCTGGGCCG CCAGACGCGC GCGGCCANGA GCATCCTGTC  550
```

FIG. 5A

```
H2-TS2cDNA  CTTCGACGCG GCCGAGTTCG ACCGCGTGCT CCGCGTCAAC GCGCTGGGCG   594
8(23)RICE   GTTCGACGCC GGGGAGTTCG ACCGCGTGCT CCGCGTCAAC GCGCTGGGCG   519
Consensus   STTCGACGCS GSSGAGTTCG ACCGCGTGCT CCGCGTCAAC GCGCTGGGCG   600

H2-TS2cDNA  CCGCGCTCGG GATGAAGCAC GCGGCGCCG CCATG----- GCGCCGCGCC    639
8(23)RICE   CCGCGCTCGG CATGAAGCAC GCGGCGCCG CCATGACCCA GCGCCGCGCC    569
Consensus   CCGCGCTCGG SATGAAGCAC GCGGCGCCG CCATGACCCA GCGCCGCGCC    650

H2-TS2cDNA  GCGCGGGGAG CATCCTCTCC GTCGCCAGCG TCGCCGCCGT GCTCGGCGGC    689
8(23)RICE   G-GC----AG CATCCTCTCC GTCGCCAGCG TCGCCGCCGT GCTCGGCGGC    614
Consensus   GCGCGGGGAG CATCCTCTCC GTCGCCAGCG TCGCCGCCGT GCTCGGCGGC    700

H2-TS2cDNA  CTCGGCCCGC ACGCCTACAC CGCCTCCAAG CACGCCATCG TCGGGCTCAC    739
8(23)RICE   CTCGGCCCGC ACGCCTACAC CGCCTCCAAG CACGCCATCG TCGGGCTCAC    664
Consensus   CTCGGCCCGC ACGCCTACAC CGCCTCCAAG CACGCCATCG TCGGGCTCAC    750

H2-TS2cDNA  CAAGAACGCC GCCTGCGAGC TGCGCGCCA CGGGGTCCGG GTCAACTGCG    789
8(23)RICE   CAAGAACGCC GCCTGCGAGC TCGCGCCCA CGGCATCCGC GTCAACTGCA    714
Consensus   CAAGAACGCC GCCTGCGAGC TSSGCGCCA CGGSRTCCGS GTCAACTGCR    800

H2-TS2cDNA  TCTCGCCCTT CGGCGTCGCC ACGCCATGC TCATCAACGC CTGGCGCCAG    839
8(23)RICE   TCTCCCCCTT CGGCGTCGCC ACGCCATGC TCATCAACGC CTGGCGCCAG    764
Consensus   TCTCSCCCTT CGGCGTCGCC ACGCCATGC TCATCAACGC CTGGCGCCAG    850

H2-TS2cDNA  GGCCACGACG ACGCCACCGC CGACGCGAC CGAGACCTCG ACCTCGACCT    889
8(23)RICE   GGCCACGACG CCTCCACCGC CGACGCG-C C--GACGCG ACCTCGACCT    811
Consensus   GGCCACGACG MCSCCACCGC CGACGCGAC CGAGACSYCG ACCTCGACCT    900

H2-TS2cDNA  CGACGTCCC GTGCCCAGCG ACCAGGAGGT GGAGAAGATG GAGGAGGTGG    939
8(23)RICE   CGACATCGCC GTGCCCAGCG ACCAGGAGGT GGAGAAGATG GAGGAGGTGG    861
Consensus   CGACRTCSCC GTGCCCAGCG ACCAGGAGGT GGAGAAGATG GAGGAGGTGG    950

H2-TS2cDNA  TCAGGGGCCT GGCCACGCTC AAGGGCCCA CGCTCAGCC CAGGGACATC    989
8(23)RICE   TCAGGGGCCT CGCCACGCTC AAGGGCGGA CGCTGAGCC CAGGGACATC    911
Consensus   TCAGGGGCCT SGCCACGCTC AAGGGCSCA CGCTSAGRCC CAGGGACATC    1000

H2-TS2cDNA  GCCGAGGCGG TGCTCTTCCT GGCCAGCGAC GAGGCCAGGT ATATATCGGG    1039
8(23)RICE   GCCGAGGCGG CGCTCTTCCT CGCCAGCGAC GACTCCAGAT ACATTTCGGG    961
Consensus   GCCGAGGCGG YGCTCTTCCT SGCCAGCGAC GASRCCAGRT AYATWTCGGG    1050

H2-TS2cDNA  CCACAACCTT GTCGTGGACG GCGGCGTCAC CACATCCAGG AACCTCATCG    1089
8(23)RICE   CCACAACCTC GTCGTCGACG GCGGCGTCAC CACCTCCAGA AACCTAATTG    1011
Consensus   CCACAACCTY GTCGTSGACG GCGGCGTCAC CACMTCCAGR AACCTMATYG    1100
```

FIG. 5B

```
H2-TS2cDNA  GCTTGTGAAT CAATGTCAAT CCGTTCCAAA T--ATCCCAT TCCCATGGCT  1137
8(23)RICE   GCCTTTGACT CTTCTTC--T CC-CTCAAGA TGAATCGAT AGTT-TAG--   1055
Consensus   GCYTNTGANT CWWTNTCANT CCGTNCCANA TGAATCCAT NSYYANNGCT  1150

H2-TS2cDNA  AGGCTAATTA GAGAAGGA-G AGAGAGAAAA CTGCTAT-TA GTTGTACTTG  1185
8(23)RICE   AACACAACTA -AAAAGGATT TGTAATGTG ACGCAACGCA AGTGTACTC-   1103
Consensus   ARSMTAANTA GAAAAGGATK NGNANNWR MKGCANYGNA NKTGTACTYG  1200

H2-TS2cDNA  AAGTGATCGA TTTTCATTTG -GTTGATTGAT TCATCAAAAA AAAAAAAAAA  1235
8(23)RICE   -AGC--TTCA -TCCATTTT GTTATCTCT TCATTCAATG TGTTAATTGG  1149
Consensus   AAGYGATYSA TTNYCATTTK GTTNATNNNT TNATTNAANR WRWWAANWRR  1250

H2-TS2cDNA  A--------- ---------- ---------- --------            1236
8(23)RICE   ACTTGTGCAA CTGAGCATTG GCCCCAAAA AAAAAAAA            1187
Consensus   ACTTGTGCAA CTGAGCATTG GCCCCAAAA AAAAAAAA            1288
```

FIG. 5C

| | | |
|---|---|---|
| 3 ORF-H2cDNA | MHASLASYAA A-AMP--ALD LRPEIAHAHQ PMMSPSHHGW DGNGATAVPT PMPKRLDGKV | 57 |
| Translation of 8(23) | MHTILASYAQ DIAMPAAALD LLPD--KAHQ PSWAPSLHAW D--SPNGAPT PMPKRLEGKV | 56 |
| Consenus | MH..LASYA. ..AMP..ALD L.P.....AHQ P.M.PS.H.W D........PT PMPKRL.GKV | 60 |
| | | |
| 3 ORF-H2cDNA | AIVTGGARGI GEAIVRLFAK HGARVVIADI DDAAGEALAS ALGPQVSFVR CDVSVEDDVR | 117 |
| Translation of 8(23) | AIVTGGARGI GEAIVRLFVK HGAKVVIADI DDAAGEALAA ALGPHVGFVR CDVSVEDVE | 116 |
| Consenus | AIVTGGARGI GEAIVRLF.K HGA.VVIADI DDAAGEALA. ALGP..FVR CDVSVE.DV. | 120 |
| | | |
| 3 ORF-H2cDNA | RAVDWALSRH GGRLDVMCNN AGVLGRQTRA ARSILSFDAA EFDRVLRVNA LGAALGMKHA | 177 |
| Translation of 8(23) | RAVERAVVRY -GRLDVLCNN AGVLGRQTRA AKSILSFDAG EFDRVLRVNA LGAALGMKHA | 175 |
| Consenus | RAV..A..R. .GRLDV.CNN AGVLGRQTRA A.SILSFDA. EFDRVLRVNA LGAALGMKHA | 180 |
| | | |
| 3 ORF-H2cDNA | ARAMAPRRAG SIVSVASVAA VLGGLGPHAY TASKHAIVGL TKNAACELRA HGVRVNQVSP | 237 |
| Translation of 8(23) | ALAMTQRRAG SIISVASVAG VLGGLGPHAY TASKHAIVGL TKNAACELGA HGIRVNQISP | 235 |
| Consenus | A.AM..RRAG SI.SVASVA. VLGGLGPHAY TASKHAIVGL TKNAACEL.A HG.RVNQ.SP | 240 |
| | | |
| 3 ORF-H2cDNA | FGVATPMLIN AWRQGHDDAT ADADRDLDLD LDVTVPSDQE VEKMEEVVRG LATLKGPTLR | 297 |
| Translation of 8(23) | FGVATPMLIN AWRQGHDAST AD--DADATID LDIAVPSDQE VEKMEEVVRG LATLKGATLR | 294 |
| Consenus | FGVATPMLIN AWRQGHD.. T AD.D.D.D LD..VPSDQE VEKMEEVVRG LATLKG.TLR | 300 |
| | | |
| 3 ORF-H2cDNA | PRDIAEAVLF LASDEARYIS GHNLVVDGGV TTSRNLIGLL | 337 |
| Translation of 8(23) | PRDIAEAALF LASDDSRYIS GHNLVVDGGV TTSRNLIGL- | 333 |
| Consenus | PRDIAEA.LF LASD. .RYIS GHNLVVDGGV TTSRNLIGL. | 340 |

FIG. 6

```
Ts2        gtg GTCAGGGG cct
ts2-m1     gtg GTCAGGGG Ac GTCAGGGG cct
Ts2-s5     gtg GTCAGG ___ GTCAGGGG cct
Ts2-s6     gtg GTCAGG ___ GTCAGGGG cct
```

5,750,873

NUCLEIC ACID MOLECULES THAT ENCODE TASSEL SEED 2(TS2), A PROTEIN INVOLVED IN THE CONTROL OF FLOWER DEVELOPMENT IN PLANTS

This application is a continuation of application Ser. No. 08/110,690, filed 23 Aug. 1993 now abandoned.

This invention was made with government support under grant number GM 38148 awarded by the National Institutes of Health. The government has certain rights in the invention.

TECHNICAL FIELD

The invention relates to agricultural and horticultural techniques for crossbreeding plants. More specifically, the invention concerns use of the tassel seed 2 (TS-2) gene to control reproductive development in plants.

BACKGROUND ART

Although most angiosperms produce flowers that carry both male and female reproductive organs, some plant species produce unisexual flowers that contain only stamens or pistils. In some of these species, those that are monoecious, flowers of each sex are produced within the same plant; in others, which are dioecious, male flowers are produced on different plants from those producing female flowers. It is known that among both monoecious and dioecious angiosperms, production of unisexual flowers is effected by aborting the development of the organs of the unwanted sex.

In maize, a programmed organ death controls the formation of the male flowers or tassels, where the cells which would otherwise form the female organs are not allowed to develop. In addition, proper formation of the female "flowers" comprising the kernels is regulated by selective destruction of half of the potential kernels to ensure proper spatial organization on the ear.

Previous workers have described mutations that affect the sexual fates of maize cells and the resultant form of the "flowers". Lesions in the tassel-seed (TS) genes cause feminization of the tassel. Phipps, I. F. *J Hered* (1928) 19:399–404; Emerson, R. A. *6th Int Cong Genet Proc* (1932) 1:141–152; and Nickerson, N. H. et al. *Ann Mol Bot Gard* (1955) 42:195–212 all report lesions in the TS gene that result in mutants which carry bisexual tassel florets. Other mutations, including the modification at the TS2 locus described herein, result in more severe feminization, as described by Emerson (1932) supra and Nickerson (1955) supra. A particular mutant of the TS2 locus, designated ts2-R reported by Emerson, R. A. *J Hered* (1920) 11:65–76 is characteristic of the particular locus which contains the transposon-tagged mutations of the present invention.

Access to the TS2 coding sequence and its promoter provides a means for controlling the sexual development of floral tissues to provide plants containing exclusively male or exclusively female flowers so as to minimize labor and expenses for plant breeding and hybrid seed production. The TS2 promoter is also useful in genetically modifying plants per se.

DISCLOSURE OF THE INVENTION

The invention provides genes which are useful in sex determination of floral tissue in angiosperms as well as tissue-specific promoters useful for recombinant production of desired materials in plants. The TS2 gene, including its promoter, from maize and from other plant species is useful in these modifications and transformations.

In one aspect, the invention is directed to isolated and purified DNA encoding the TS2 gene product of maize or of other angiosperms and to expression systems for production of this gene product suitable for modifying plants.

In another aspect, the invention is directed to antisense materials capable of interfering with the expression of the TS2 gene.

In still other aspects, the invention concerns methods to employ the TS2 promoter for recombinant production of materials in plants and to plant cells in plants modified with the foregoing materials.

BRIEF DESCRIPTION OF THE DRAWINGS

FIGS. 3A–B shows the nucleotide sequence (SEQ ID NO:1) of a maize cDNA clone which contains the open reading frame encoding the TS2 gene product.

FIGS. 4A–B shows the nucleotide sequence (SEQ ID NO:2) and deduced amino acid sequence of a cDNA derived from rice encoding the TS2 related product.

FIGS. 5A–C shows a comparison of aligned nucleotide sequences (SEQ ID NO:1 and SEQ ID NO:2) of maize and rice cDNA clones of TS2 gene products wherein the maize sequence is identified by "H2-TS2cDNA" and the rice sequence as identified by "8(23)".

FIG. 6 shows a comparison of the amino acid sequences (SEQ ID NO:3 and SEQ ID NO:4) deduced from the genes of FIG. 5 wherein the maize sequence is identified by "H2-TS2cDNA" or SEQ ID NO:3 and the rice sequence as identified by "8(23)" or SEQ ID NO:4.

MODES OF CARRYING OUT THE INVENTION

The TS2 gene and related genes in other plants are provided by the invention. The structures of the TS2 gene in maize and rice are similar and considerable consensus is observed between both the DNA sequences and the encoded proteins. The proteins encoded by both genes share considerable amino acid sequence similarity with bacterial members of the short chain alcohol dehydrogenase family, particularly with hydroxysteroid dehydrogenases.

Figure 1:
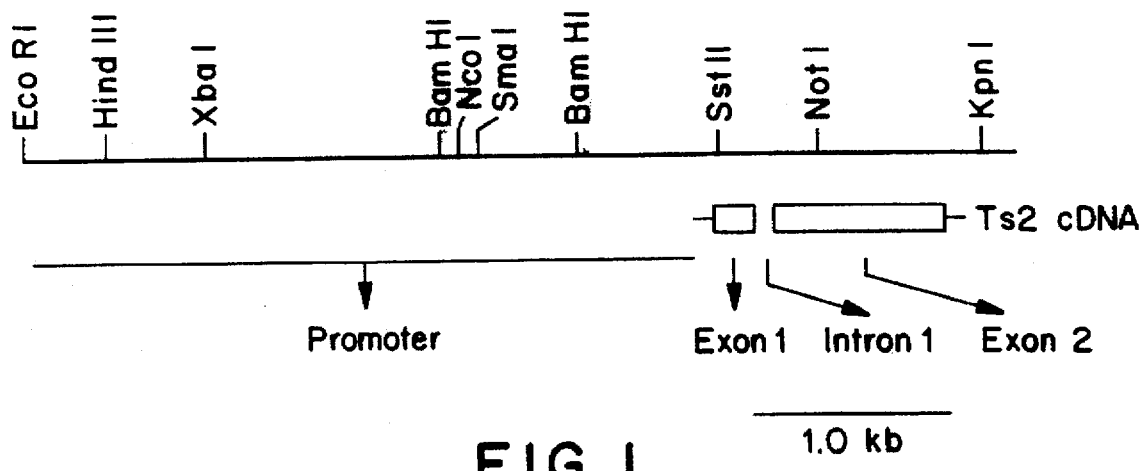
FIG. 1 is a diagrammatic representation of the maize TS2 gene structure.
Figure 2:
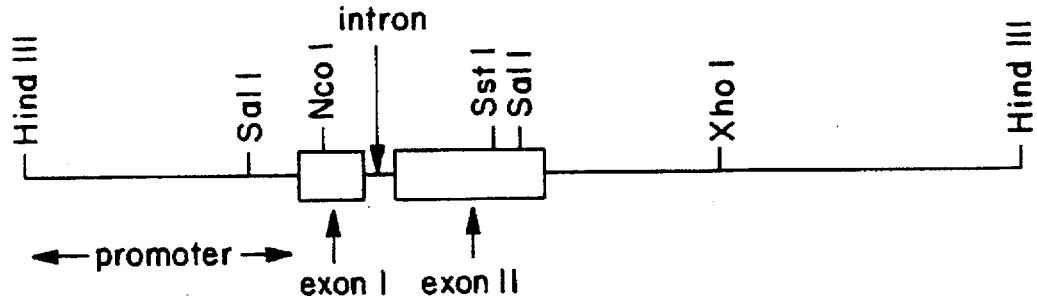
FIG. 2 is a diagrammatic representation of the TS2 related gene derived from rice.

The general structures of the maize TS2 gene and of the rice TS2 gene are shown in FIGS. 1 and 2 respectively. As seen, both contain a single intron in the coding sequences. As used herein the "TS2 gene" refers to the nucleotide sequence at the locus which effects the production of the protein product described herein as similar to a small molecule dehydrogenase. The gene includes not only the open reading frame encoding the gene product, but also the transcription and translation regulatory sequences associated with this locus. Thus, the "TS2 gene" includes the promoter, initiation and termination signals for message and for translation, and any other cis-acting controls.

FIGS. 3A–3B shows the complete cDNA nucleotide sequence for the H2 clone containing the entire open reading frame of the maize TS2-encoded protein. The start codon is preceded by the arrow prior to nucleotide 87 in the figure. The cDNA clone was obtained as described herein, and the amino acid sequence of the relevant product can be deduced from the nucleotide sequence.

FIG. 4 shows the complete nucleotide sequence and deduced amino acid sequence of the gene encoding the rice protein related to the maize protein encoded by the DNA of FIG. 3. FIGS. 5A, 5B and 5C shows the alignment of the H2 TS2 DNA clone with the rice TS2 related cDNA; FIG. 6 shows the alignment of the deduced amino acid sequences.

As seen, the homology of the nucleotide and the amino acid sequences of these loci in disparate species of plants indicates that the genes derived from rice or maize and the nucleic acid sequences associated with the gene and its regulatory regions will be applicable and functional in additional plants; in addition, DNA derived from rice or maize will be useful in retrieving the corresponding DNA in additional species.

As used herein, "derived from" means that the structural characteristics of the subject are based on those of the referrant. The term includes, but is not limited to physical derivation. Thus, nucleotide sequences "derived from" a native DNA may be synthetically prepared but are ordered so as to correspond to the native sequences. Where applicable, "derived from" also includes degenerate sequences. The contexts in which degenerate sequences are applicable are well known to those in the art.

Thus, in one embodiment of the practice of the invention, the coding region of the appropriate TS2 locus under the control of its own promoter or under the control of heterologous sequences is inserted into host plants to control the sex of the flowers produced by the transformed plant. Control sequences that are functional either constitutively or in the relevant functional tissues in plants are employed.

Transcription initiation regions, for example, include the various opine initiation regions, such as octopine, mannopine, nopaline and the like. Plant viral promoters can also be used, such as the cauliflower mosaic virus 35S promoter. In addition, plant promoters such as ribulose-1,3-diphosphate carboxylase, fruit-specific promoters, heat shock promoters, seed-specific promoters, etc. can also be used. A large number of suitable control systems is available. For example, the cauliflower mosaic virus (CaMV) 35S promoter has been shown to be highly active in many plant organs and during many stages of development when integrated into the genome of transgenic plants including tobacco and petunia, and has been shown to confer expression in protoplasts of both dicots and monocots.

Organ-specific promoters are also well known. For example, the E8 promoter is only transcriptionally activated during tomato fruit ripening, and can be used to target gene expression in any system wherein ethylene activates biological processes.

Other organ-specific promoters appropriate or a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, *Trans R Soc London* (1986) B314:343.

These mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al., *Plant Molecular Biology* (1984) 3:385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

A somewhat more sophisticated procedure was described in *Molecular Biology of the Cell*, Second Edition (1989) pages 261–262, edited by Alberts et al., Garland Publishing Incorporated, New York. In this procedure, mRNAs enriched for organ-specific nucleic acid sequences were used to construct the cDNA library.

The gene that encodes the organ-specific mRNA is then isolated by constructing a library of DNA genomic sequences from the plant. The genome library is screened with the organ-specific cDNA clone, and the sequence is determined. The promoter is then isolated. These procedures are now considered to be routine and are described in detail in Sambrook et al., *Molecular Cloning: A Laboratory Manual*, Second Edition (1989) Cold Spring Harbor Laboratory Press, Cold Spring Harbor.

Either a constitutive promoter (such as the CaMV or Nos promoter illustrated above) or a desired organ-specific promoter (such as the E8 promoter from tomato or alternate specific promoter isolated using organ-specific cDNA as described above) is then ligated to the gene encoding the TS2 gene product using standard techniques now common in the art. The expression system may be further optimized by employing supplemental elements such as transcription terminators and/or enhancer elements.

Thus, for expression in plants, the recombinant expression cassette will contain in addition to the coding sequence, a plant promoter region, a transcription initiation site and a transcription termination sequence. Unique restriction enzyme sites at the 5' and 3' ends of the cassette are typically included to allow for easy insertion into a preexisting vector.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the Agrobacterium octopine synthase signal (Gielen et al., *EMBO J* (1984) 3:835–846) or the nopaline synthase signal (Depicker et al., *Mol and Appl Genet* (1982) 1:561–573).

The resulting expression system or cassette is ligated into or otherwise constructed to be included in a recombinant vector which is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range procaryotic origin of replication is included. A selectable marker for bacteria should also be included to allow selection of bacterial cells bearing the desired construct. Suitable procaryotic selectable markers also include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

In addition, vectors can also be constructed that contain in-frame ligations between the sequence encoding the TS-encoded protein and sequences encoding other molecules of interest resulting in fusion proteins, by techniques well known in the art.

When an appropriate vector is obtained, transgenic plants are prepared which contain the desired expression system. A number of techniques are available for transformation of plants or plant cells. All types of plants are appropriate subjects for "direct" transformation; in general, until recently only dicots could be transformed using Agrobacterium-mediated infection.

In one form of direct transformation, the vector is microinjected directly into plant cells by use of micropipettes to mechanically transfer the recombinant DNA (Crossway, *Mol Gen Genetics* (1985) 202:179–185). In another form, the genetic material is transferred into the plant cell using polyethylene glycol (Krens, et al., *Nature* (1982) 296:72–74), or high velocity ballistic penetration by small particles with the nucleic acid either within the matrix of small beads or particles, or on the surface, is used (Klein, et al., *Nature* (1987) 327:70–73). In still another method protoplasts are fused with other entities which contain the DNA whose introduction is desired. These entities are minicells, cells, lysosomes or other fusible lipid-surfaced bodies (Fraley, et al., *Proc Natl Acad Sci USA* (1982) 79:1859–1863).

DNA may also be introduced into the plant cells by electroporation (Fromm et al., *Proc Natl Acad Sci USA* (1985) 82:5824). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

For transformation mediated by bacterial infection, a plant cell is infected with *Agrobacterium tumefaciens* or *A. rhizogenes* previously transformed with the DNA to be introduced. Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (Schell, J., *Science* (1987) 237:1176–1183). Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid (Hoekema, et al., *Nature* (1983) 303:179–189). The transferred DNA region can be increased in size by the insertion of heterologous DNA without its ability to be transferred being affected. Thus a modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors," (Ruvkum and Ausubel, *Nature* (1981) 298:85–88), promoters (Lawton et al., *Plant Mol Biol* (1987) 9:315–324) and structural genes for antibiotic resistance as a selection factor (Fraley et al., *Proc Natl Acad Sci* (1983) 80:4803–4807).

There are two classes of recombinant Ti and Ri plasmid vector systems now in use. In one class, called "cointegrate," the shuttle vector containing the gene of interest is inserted by genetic recombination into a non-oncogenic Ti plasmid that contains both the cis-acting and trans-acting elements required for plant transformation as, for example, in the pMLJ1 shuttle vector of DeBlock et al., *EMBO J* (1984) 3:1681–1689 and the non-oncogenic Ti plasmid pGV3850 described by Zambryski et al., *EMBO J* (1983) 2:2143–2150. In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* (1984) 12:8711–8721 and the non-oncogenic Ti plasmid PAL4404 described by Hoekma, et al., *Nature* (1983) 303:179–180. Some of these vectors are commercially available.

There are two common ways to transform plant cells with Agrobacterium: co-cultivation of Agrobacterium with cultured isolated protoplasts, or transformation of intact cells or tissues with Agrobacterium. The first requires an established culture system that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants.

Most dicot species can be transformed by Agrobacterium as all species which are a natural plant host for Agrobacterium are transformable in vitro. Monocotyledonous plants, and in particular, cereals, are not natural hosts to Agrobacterium. Attempts to transform them using Agrobacterium have been unsuccessful until recently (Hooykas-Van Slogteren et al., *Nature* (1984) 311:763–764). However, there is growing evidence now that certain monocots can be transformed by Agrobacterium. Using novel experimental approaches cereal species such as rye (de la Pena et al., *Nature* (1987) 325:274–276), maize (Rhodes et al., *Science* (1988) 240:204–207), and rice (Shimamoto et al., *Nature* (1989) 338:274–276) may now be transformed.

Identification of transformed cells or plants is generally accomplished by including a selectable marker in the transforming vector, or by obtaining evidence of successful bacterial infection.

Plant cells which have been transformed can also be regenerated using known techniques.

Plant regeneration from cultured protoplasts is described in Evans et al., *Handbook of Plant Cell Cultures*, Vol. 1: (MacMillan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

A large number of plants have been shown capable of regeneration from transformed individual cells to obtain transgenic whole plants. The transgenic plant containing the coding region for the TS2 gene then is expected to produce predominantly male flowers. This facilitates crossbreeding with plants, especially, which contain female flowers exclusively.

Plants bearing only female flowers can be produced by taking advantage of the availability of the DNA associated with the TS2 locus to construct antisense sequences for interruption of expression of the TS2 gene. As evidenced by the behavior of TS2 mutants in maize, failure of the endogenous TS2 gene to be expressed results in feminization of the floral organs. Accordingly, antisense sequences of suitable length are transfected into plant cells using the methods described above to result in plants bearing female flowers.

Finally, the TS2 promoter region is of general utility in effecting recombinant production of desired products and plants. The TS2 promoter can be used to effect expression of various foreign genes in root tissue, for example.

EXAMPLES

The following examples are intended to illustrate but not to limit the invention. A few general comments may be in order concerning the examples below. The wild-type TS2 allele is designated TS2. Alleles generically that complement the mutant ts2-R are designated Ts2. Alleles that fail to complement ts2-R are designated ts2. Alleles generated by Ac excision from ts2-m1 are collectively designated Ts2*.

Figure 7:
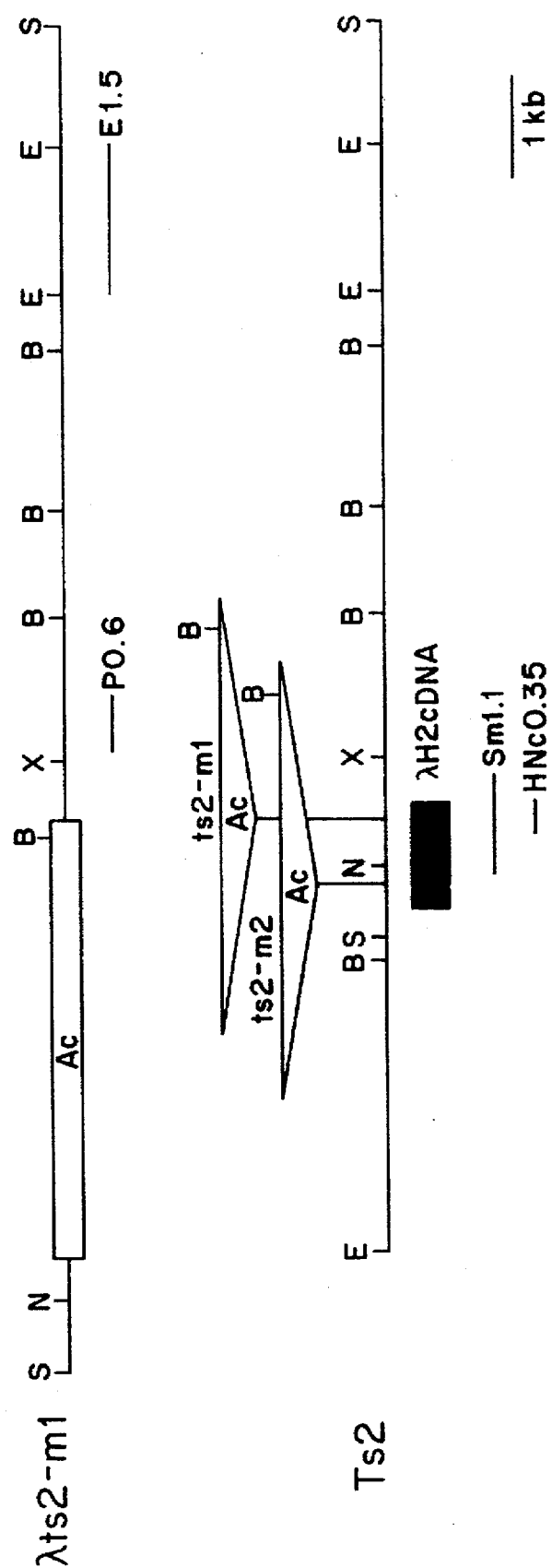
FIG. 7 shows a diagram of the mutant TS2 loci of the invention and the location of probes PO.6, E1.5, SM1.1, and HNc0.35 used in the illustrative procedures reported herein.

Wild-type control lines with respect to the tasselseed locus were W22 and Ts24Co63. Probes used in the various examples described hereinbelow are illustrated in FIG. 7 with respect to their locations in the transposon-mutated and wild-type loci.

Example 1

Use of Tasselseed Mutations to Obtain the TS2 Locus

The Ac gene tagging strategy described by Dellaporta, S. L. and Moreno, M. A. "Maize Handbook", M. Freling and V. Walbot, Eds. (1993) Springer-Verlag, New York, was used to isolate TS2 loci containing mutations associated with Ac transposition events. Each such mutation causes feminization of the tassels, which then produce only female florets. In addition, each mutation results in irregularly spaced kernels due to overcrowding. In normal development, each kernel develops from a pair of primordia and the presence of an active TS2 locus evidently results in the abortion of one of the primordia, permitting regular spacing of the kernels in nonmutants. In mutants, such abortion is prevented.

The Ac transposon mutants are recessive and linked to the P locus on chromosome 1; these mutants are designated ts2-m1 and ts2-m2 herein and are incapable of complementing the above-referenced known ts2-R allele.

The homozygous ts2-m1 plants often exhibit revertants which suggests that the mutation may be caused by insertion of a transposable element. Male sectors on ts2-m1 plants shed viable pollen indicating that revertant florets are sexually functional, and there is a wide range of revertant sector sizes including many single and multiple spikelet sectors. The occurrence of single revertant spikelets suggests that restored action of the TS2 locus can alter the sexual fate of the floral primordium quite late in development.

Figure 9A:
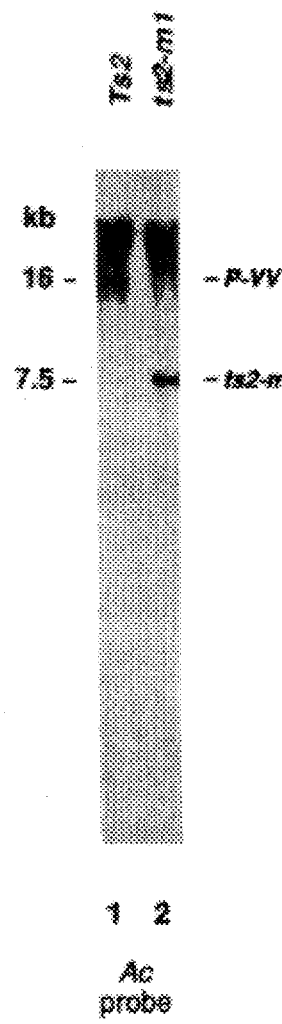
FIGS. 9A–C shows Southern Blots of wild-type and mutant genomic DNA detected with various probes.
Figure 9B:
Figure 9C:
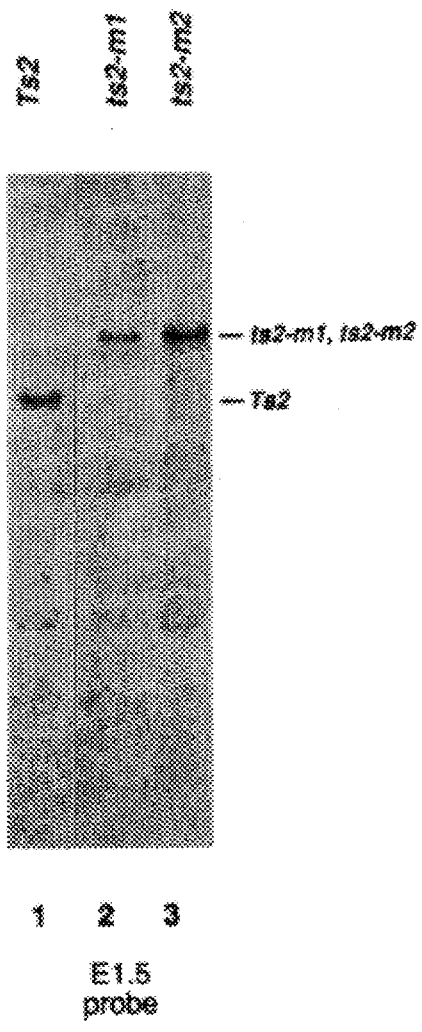

Plants carrying the ts2-m1 allele carry an active Ac element showing linkage to ts2-m1 in segregating families. It is known that PstI does not cleave within Ac sequences, and in ts2-m1 DNA, an Ac probe recognized a hypomethylated 7.5 kbp PstI fragment absent from DNA extracted from the parental line which does not contain the ts2-m1 mutation. See part A of FIG. 9. The 7.5 kbp PstI fragment was present in 32 DNA samples from individual plants homozygous for the ts2-m1 allele.

A genomic library from a plant homozygous for ts2-m1 was screened using the Ac probe. One clone, λts2-m1, was recovered which contained a single 14 kb SstI fragment which hybridized with the Ac probe and comigrated with the SstI fragment in its ts2-m1 genomic DNA. Sequences flanking the Ac element in λts2-m1 were used as probes in Southern Blot analysis DNA from mutant and wild-type plants. See FIG. 7 for the locations of these probes to verify the identity of the cloned DNA. In ts2-m1 genomic DNA, 0.6 kb XhoI/PstI (PO.6) flanking probe detected the 7.5 kb PstI fragment previously identified using the Ac probe. In wild-type DNA, the flanking probe hybridized to a 2.9 kb PstI fragment. This is consistent with insertion of a full-length Ac element (4.56 kb) into the parental 2.9 kb PstI fragment. (See FIG. 9, parts A and B.)

Flanking probes isolated from λts2-m1 were also used to map the Ac insertion in the ts2-m2 allele by subjecting a DNA from ts2-m2 plants to Southern Blot. Again, ts2-m2 contained an SstI fragment roughly 4.6 kb larger than the 9 kb parental fragment. See FIG. 9, part C. Additional mapping experiments confirmed the Ac insertion sites in the two alleles are separated by about 600 bp. A diagram of the two mutants indicating the site of insertion of the Ac segment is shown in FIG. 7. In FIG. 7, PO.6 indicates the probe used to analyze Southern Blots from ts2-m1; E1.5 indicates the probe used to analyze the Southern Blots in ts2-m2.

The 14 kb SstI fragment that hybridized to the Ac probe and cosegregated with the ts2-m1 mutation was used to isolate the TS2 locus. DNA extracted from homozygous ts2-m1 mutant plants was constructed in λDASHII (stratagene) and screened using the central 1.6 kb Hind-III fragment of Ac as a probe as described by Federoff, N. V. "Mobile DNA", Howe and Berg, Eds. (1989) Washington, D.C. Am Soc Microbiol, pp. 377–411. Plasmid pADL-101 contains the AccI end of Ac and the 1.2 kb flanking TS2 DNA; pADL-103 contains the large EcHoR1 fragment spanning the BamHI end of Ac and 5 kb of its TS2 DNA. See FIG. 7. After partial Sau3A digestion of W22 DNA, a TS2 genomic library was generated in λDASHII and screened with a probe spanning the SstI/NotI fragment in λts2-m1. Plasmids pADL-170 and pADL-171 carry the HNc 0.35 fragment in opposite orientations in vector pTZ 19 (U.S. Biochemical). See FIG. 7 for its location. For cloning the Ac excision sites from Ts2* alleles, Ts2* homozygotes were identified by Southern Blot analysis and genomic DNA was used to generate λZAP (Stratagene) libraries which were screened with the PO.6 probe. Clones carrying the appropriate 2.5 kb SstI/XbaI inserts were purified and plasmid subclones pAD114 and pADL115 were rescued in vivo and sequenced.

Example 2

Recovery of cDNA Encoding the Ts2 Gene Product

A cDNA library constructed using the Time Saver Plus Kit (Pharmacia) was screened with the HNc0.35 probe. The largest TS2 cDNA clone, pADL2-11 which contains a 1.0 kb insert was used to screen a second similarly constructed library from which the 1.2 kb H2 clone was isolated. The sequence of the H2 clone is shown in FIG. 3. The organization of H2 and other cDNA clones was consistent with the direction of TS2 transcription inferred from in situ hybridization and RACE results. There was one 1011 bp open reading frame beginning with the first ATG present in the sequence and ending with the TGA 123 bp upstream from the beginning of the poly-A tail. The molecular weight of the product is 35 kb and a predicted pI is 6.7; the complete deduced amino acid sequence is shown in comparison to the corresponding rice protein in FIG. 6.

Example 3

Determination of Location of Expression

Inbred w2 was the wild-type Ts2 used.

For in situ hybridization, formaldahyde tissue fixation, paraffin embedding, microtomy, and slide pretreatment procedures were standard. Ribroprobes were T7 transcripts of ECORI digested pADL 170 (HNcO.35B) and pADL 171 (HNcO.35T). PMC56 (Stiefel, V et al. Plant Mol Biol (1988) 11:483–493 was used as a control. The probes were labeled with 11-digoxigenin dUTP and probehydrolysis was according to Langdale J. A. et al Genes Dev (1988) 2:106–115. Sections were prehyberdized for 1–2 hours at 22° C. in 220 µl hybridization solution and hybridized overnight at 50° C. according to Langdale et al except the final probe concentration was 0.5 λg/ml/kb. Generally standard washing and development procedures were followed.

The occurrence of small revertant sectors on ts2-m1 mutant plants indicates that TS2 may act relatively late in inflorescence development. However no Ts2 message from immature tassels could be found.

In situ hybridization was used to detect expression of the TS2 gene. Immature tassels were collected at various developmental stages and subjected to in situ hybridization using single-stranded RNA probes. The preservation of reading frame in the Ts2-s5 and Ts2-s6 alleles suggested the choice of a probe spanning the site of the ts2-m1 Ac insertion. Digoxigenin-labeled RNA transcripts corresponding to the top (HNcO.35T) and bottom (HNc).35B) strnads of probe HNc0.35 were generated. Probe HNc0.35B detected a message in florets bearing distinct floral organ primordia and this was strongest in a group of subepidermal cells in the gynoecium. When serial sections or comparable sections of ts2-m1 tassels were hybridized to probe HNcO.35T, no hybridization above background levels was detected. Thus the Ts2 message is transcribed from left to right, relative to the map shown in FIG. 7, and sequences in the 350 bp flanking the ts2-m1 Ac insertion site are transcribed in developing wild-type tassels but not in ts2-m1 mutant tassels. Hybridization of identical tassel sections with pMC56, transcripts used as a control gave a strong signal in vascular traces in the main and branch axes, and in developing floral organs and floral primordi. This result indicates that the gynoecium is still a rapidly growing primordium when TS2 expression occurs. Hybridization of pMC56 transcripts to organ primordia in sections of ts2-m1 mutant tassels also was observed. The signal obtained with pMC56 was well above that observed with HNcO.35B, which is consistent with the hypothesis that the abundance of the Ts2 message is low.

To confirm the data obtained through in situ hybridization, we used the "rapid amplification of cDNA ends" (RACE) method to detect expression of the TS2 gene. Total RNA was isolated by guanidine thiocyanate extraction from the wild-type strain W22 containing the TS2 locus. RNA was treated with RNA-ase-free DNA-aseI for 20 minutes at 37° C. and poly-A$^+$ RNA purified on Dynabeads. The RACE procedure of Frohman, M. A. et al. Proc Natl Acad Sci USA (1988) 85:8998–9002 was used with modifications. The template for reverse transcription was 100 ng poly-A$^+$ RNA; after treatment with AMV reverse transcriptase, the reaction mixture was diluted to a final volume of 100 µl. The adapter primer and TS2 specific primer were used for PCR amplification; the initial denaturation, annealing and extension steps were 95° C., 3 min; 56° C., 40 sec; 72° C., 5 min (one cycle), followed by 95° C., 40 sec; 56° C., 1 min; 72° C., 2 min for 39 cycles. An oligonucleotide sequence internal to the HNc0.35 probe and identical to the putative sense strand of the TS2 gene was chosen for the TS2 primer. Total RNA was isolated from immature Ts2 and ts2-R tassels, and was treated DNase to remove any residual genomic DNA. Poly-A$^+$ RNA was purified, annealed with a RACE-poly-dT adaptor-primer, and treated with reverse transcriptase to produce cDNA. Each cDNA sample was subjected to polymerase chain reaction (PCR) amplification using a TS2-specific primer and the adaptor primer. The amplification products were subjected to Southern blot analysis, using a probe that spans the ts2-m1 Ac insertion site (Sm1.1; FIG. 7). A single 450 bp product was detected in the amplification products of the Ts2 cDNA population. This product was not amplified when genomic Ts2 DNA or Ts2 RNA (without reverse transcriptase treatment) was used as template nor when ts2-R cDNA was used as template in the PCR reaction. These results are consistent with the data obtained via in situ hybridization.

Example 4

Excision of AC from Ts2-m1 to Effect Revertants

Pollen from three independent revertant tassel sectors was used to pollinate Ts2/Ts2 females. Southern blot analysis of DNA from the test-cross offspring showed that 7/16 progeny did not carry the 14 kb SstI fragment characteristic of ts2-m1, but a 9.1 kb SstI fragment (Ts2*) that co-migrated with the wild-type fragment. The results for 4 of these offspring are shown in lanes 3–6 of FIG. 8A. (Lane 1 represents the parent Ts-2; lane 2 represents ts2-m1). Both the internal 1.6 kb Ac probe and the PO.6 flanking probe were used. The remaining 9/16 progeny did carry the ts2-m1 14 kb SstI fragment in addition to the maternally donated 9.1 kb Ts2 fragment; data not shown. Further mapping experiments confirm that Ac is absent from the Ts2* SstI fragment (data not shown). Thus two kinds of gametes were produced in the revertant sector: one gamete carrying the ts2-m1 allele, and the other carrying a Ts2* allele apparently created by excision of Ac from ts2-m1. Similar results were obtained with test-cross progeny from each revertant sector (data not shown). Thus, the λts2-m1-derived PO.6 probe detected excision of Ac from the ts2-m1 allele, and such excision events resulted in sexual transformation of both somatic and germinal tassel tissues.

Excision as well as insertion, of Ac is mutagenic. Insertion events create an 8-bp target site duplication, and excision is imprecise, generally leaving sequence alteration at the target site. If Ac disrupts an exon, only excision events that restore the reading frame are likely to restore gene function, yielding a phenotypically revertant sector. The nucleotide sequences 1) flanking Ac in λts2-m1, 2) the corresponding sequence present in the wild-type Ts2 allele, and 3) the sequences present in two independent alleles recovered from revertant tassel sectors, Ts2-s5 and Ts2-s6 were all sequenced.

Figures 8A, 8B:
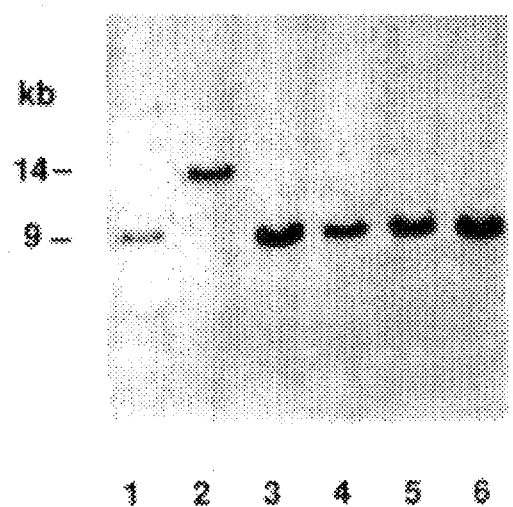
FIG. 8a shows a Southern Blot of wild-type, mutant, and revertant genomic DNA.
FIG. 8b shows the sequences (SEQ ID NO:5, SEQ ID NO:6 and SEQ ID NO:7) adjoining the Ac insert in the transposon modified mutants of the invention.

FIG. 8B shows the results. The Ac element in ts2-m1 was flanked by a target site duplication of 8 bp. The Ts2-s5 and Ts2-s6 alleles carried an identical six base-pair insertion not found in the wild-type; this 6 bp insertion preserves the open reading frame present in this region (see below). Although Ts2-s5 and Ts2-s6 restore sufficient Ts2 function to create somatic sectors, they do not behave as true revertant alleles. They complement ts2-R only weakly. New Ts2 alleles were thus generated by excision of Ac from the ts2-m1 allele. The identical excision site sequences and the partial revertant phenotypes of Ts2-s5 and Ts2-s6 indicate that relatively few excision events can create revertant or partial revertant alleles.

---

I claim:

1. An isolated nucleic acid molecule that encodes a protein with an amino acid sequence selected from the group consisting of SEQ ID NO:3 (maize Tassel Seed 2 (TS2) gene product), SEQ ID NO:4 (rice TS2 gene product), and SEQ ID NO:8 (consensus TS2 gene product).

2. The nucleic acid molecule of claim 1 wherein the nucleotide sequence of said nucleic acid molecule is selected from the group consisting of SEQ ID NO:1, SEQ ID NO:2, and SEQ ID NO:9.

3. A vector that comprises the nucleic acid molecule of claim 1.

4. A vector that comprises the nucleic acid molecule of claim 2.

5. The nucleic acid molecule of claim 1 operably linked to one or more nucleotide sequences selected from the group consisting of promoter sequences, transcription terminator sequences, and enhancer sequences.

6. The nucleic acid molecule of claim 2 operably linked to one or more nucleotide sequences selected from the group consisting of promoter sequences, transcription terminator sequences, and enhancer sequences.

7. A plant or microbial cell that has been transformed to contain the nucleic acid molecule of claim 1.

8. A plant or microbial cell that has been transformed to contain the nucleic acid molecule of claim 2.

9. A plant or microbial cell that has been transformed to contain the nucleic acid molecule of claim 5.

10. A plant or microbial cell that has been transformed to contain the nucleic acid molecule of claim 6.

11. The cell of claim 9 wherein said recombinant host cell is a plant cell.

12. The cell of claim 10 wherein said recombinant host cell is a plant cell.

13. A plant regenerated from the cell of claim 11.

14. A plant regenerated from the cell of claim 12.

15. The plant cell of claim 11 wherein said plant cell is obtained from a dicotyledenous plant.

16. The plant cell of claim 12 wherein said plant cell is a obtained from a dicotyledenous plant.

17. An isolated nucleic acid molecule from an angiosperm that hybridizes to a nucleotide sequence selected from the group consisting of SEQ ID NO:1, SEQ ID NO:2, and SEQ ID NO:9, under high stringency so as to produce a selective and detectable signal and said nucleic acid molecule encodes a protein that has the biological activity of the TS2 protein from maize or rice.

18. A vector that comprises the nucleic acid molecule of claim 17.

19. The nucleic acid molecule of claim 17 operably linked to one or more nucleotide sequences selected from the group consisting of promoter sequences, transcription terminator sequences, and enhancer sequences.

20. A plant or microbial cell that has been transformed to contain the nucleic acid molecule of claim 17.

21. A plant or microbial cell that has been transformed to contain the nucleic acid molecule of claim 19.

22. The cell of claim 20 wherein said recombinant host cell is a plant cell.

23. The cell of claim 21 wherein said recombinant host cell is a plant cell.

24. A plant regenerated from the cell of claim 22.

25. A plant regenerated from the cell of claim 23.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1236 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
CACGCACTCG  CCTCTTGTGT  CTTTCTTTGT  GAGCTGTGGT  GTGGTGGTCG  AGACACACAC       60

AGCAGCAGCA  ACAACAACAT  ACATACATGC  ACGCTAGCCT  CGCCTCCTAC  GCCGCGGCAG      120

CTATGCCGGC  GCTGGACCTC  CGCCCCGAGA  TAGCGCACGC  GCACCAGCCC  GTCATGTCGC      180

CCTCTCACCA  CGGCTGGGAC  GGCAATGGCG  CCACAGCCGT  GCCCACACCG  ATGCCCAAGA      240

GGCTGGACGG  GAAGGTGGCC  ATTGTGACGG  GCGGCGCGCG  CGGGATCGGC  GAGGCCATCG      300

TGCGGCTGTT  CGCCAAGCAC  GGGGCCCGGG  TGGTGATCGC  GGACATCGAC  GACGCCGCGG      360

GGGAGGCGCT  GGCGTCGGCG  CTGGGCCCGC  AGGTCAGCTT  CGTGCGCTGC  GACGTGTCCG      420

TGGAGGACGA  CGTCCGGCGC  GCCGTGGACT  GGGCGCTGTC  GCGCCACGGC  GGCCGCCTCG      480

ACGTCTACTG  CAACAACGCC  GGGGTGCTGG  GCCGCCAGAC  GCGCGCGGCC  AGGAGCATCC      540

TGTCCTTCGA  CGCGGCCGAG  TTCGACCGCG  TGCTCCGCGT  CAACGCGCTG  GGCGCCGCGC      600

TCGGGATGAA  GCACGCCGCG  CGCGCCATGG  CGCCGCGCCG  CGCGGGGAGC  ATCGTCTCCG      660

TCGCCAGCGT  CGCGGCCGTG  CTGGGCGGCC  TCGGCCCGCA  CGCCTACACC  GCCTCCAAGC      720

ACGCCATCGT  CGGGCTCACC  AAGAACGCCG  CCTGCGAGCT  GCGCGCGCAC  GGGGTCCGGG      780
```

| | | | | | |
|---|---|---|---|---|---|
| TCAACTGCGT | CTCGCCCTTC | GGCGTCGCCA | CGCCCATGCT | CATCAACGCC | TGGCGCCAGG | 840
| GCCACGACGA | CGCCACCGCC | GACGCCGACC | GAGACCTCGA | CCTCGACCTC | GACGTCACCG | 900
| TGCCCAGCGA | CCAGGAGGTG | GAGAAGATGG | AGGAGGTGGT | CAGGGGCCTG | GCCACGCTCA | 960
| AGGGCCCCAC | GCTCAGGCCC | AGGGACATCG | CCGAGGCGGT | GCTCTTCCTG | GCCAGCGACG | 1020
| AGGCCAGGTA | TATATCGGGC | ACAACCTTG | TCGTGGACGG | CGGCGTCACC | ACATCCAGGA | 1080
| ACCTCATCGG | CTTGTGAATC | AATGTCAATC | CGTTCCAAAT | ATCCCATTCC | CATGGCTAGG | 1140
| CTAATTAGAG | AAGGAGAGAG | AGAAAACTGC | TATTAGTTGT | ACTTGAAGTG | ATCGATTTTC | 1200
| ATTTGGTTGA | TTGATTCATC | AAAAAAAAAA | AAAAA | | | 1236

( 2 ) INFORMATION FOR SEQ ID NO:2:

( i ) SEQUENCE CHARACTERISTICS:
( A ) LENGTH: 1187 base pairs
( B ) TYPE: nucleic acid
( C ) STRANDEDNESS: single
( D ) TOPOLOGY: linear ( x i ) SEQUENCE DESCRIPTION: SEQ ID NO:2:

| | | | | | |
|---|---|---|---|---|---|
| CTAGGACAGG | GTCGTACATG | CACACTACCC | TCGCCTCCTA | CGCCCAGGAT | CTCGCCATGC | 60
| CTGCCGCCGC | ACTCGACCTC | CTCCCTGACA | AGGCGCACCA | GCCGTCCATG | GCGCCGTCGC | 120
| TCCACGCCTG | GGACTCCCCC | AATGGCGCCC | CCACTCCCAT | GCCCAAGAGG | CTGGAAGGGA | 180
| AGGTGGCCAT | TGTCACCGGC | GGGGCGAGGG | GGATCGGGGA | GGCGATCGTG | AGGCTGTTCG | 240
| TTAAGCACGG | GGCCAAGGTG | GTGATCGCGG | ACATCGACGA | CGCGGCGGGC | GAGGCGCTGG | 300
| CGGCGGCGCT | GGGGCCGCAC | GTCGGGTTCG | TGCGGTGCGA | CGTGTCGGTG | GAGGAGGACG | 360
| TGGAGCGCGC | CGTCGAGCGC | GCCGTGGCGC | GGTACGGGCG | GCTGGACGTG | CTGTGCAACA | 420
| ACGCCGGGGT | GCTGGGCCGC | CAGACGCGCG | CCGCCAAGAG | CATCCTGTCG | TTCGACGCCG | 480
| GGGAGTTCGA | CCGCGTGCTC | CGCGTCAACG | CGCTGGGCGC | CGCGCTCGGC | ATGAAGCACG | 540
| CGGCGCTCGC | CATGACCCAG | CGCCGCGCCG | GCAGCATCAT | CTCCGTCGCC | AGCGTCGCCG | 600
| GCGTGCTCGG | CGGCCTCGGC | CCGCACGCCT | ACACCGCCTC | CAAGCACGCC | ATCGTGGGGC | 660
| TCACCAAGAA | CGCCGCCTGC | GAGCTCGGCG | CCCACGGCAT | CCGCGTCAAC | TGCATCTCCC | 720
| CCTTCGGCGT | CGCCACCCCG | ATGCTCATCA | ACGCCTGGCG | CCAGGGCCAC | GACGCCTCCA | 780
| CCGCCGACGA | CGCCGACGCC | GACATCGACC | TCGACATCGC | CGTGCCCAGC | GACCAGGAGG | 840
| TGGAGAAGAT | GGAGGAGGTG | GTCAGGGGCC | TCGCCACGCT | CAAGGGCGCG | ACGCTGAGAC | 900
| CCAGGGACAT | CGCCGAGGCG | GCGCTCTTCC | TCGCCAGCGA | CGACTCCAGA | TACATTTCCG | 960
| GCCACAACCT | CGTCGTCGAC | GGCGGCGTCA | CCACCTCCAG | AAACCTAATT | GGCCTTTGAC | 1020
| TCTTCTTCTC | CCTCTAGATG | AATGCGATAG | TTTAGAACAC | AACTAAAAAG | GATTTGTTAA | 1080
| TGTGACGCAA | CGCAAGTGTA | CTCAGCTTCA | TCCCATTTTG | TTAATCTCTT | GATTCAATGT | 1140
| GTTAATTGGA | CTTGTGCAAC | TGAGCATTGG | CCCCCAAAAA | AAAAAA | | 1187

( 2 ) INFORMATION FOR SEQ ID NO:3:

( i ) SEQUENCE CHARACTERISTICS:
( A ) LENGTH: 337 amino acids
( B ) TYPE: amino acid
( C ) STRANDEDNESS: single
( D ) TOPOLOGY: linear ( x i ) SEQUENCE DESCRIPTION: SEQ ID NO:3:

| Met | His | Ala | Ser | Leu | Ala | Ser | Tyr | Ala | Ala | Ala | Ala | Met | Pro | Ala | Leu |
|---|---|---|---|---|---|---|---|---|---|---|---|---|---|---|---|
| 1 | | | | 5 | | | | | 10 | | | | | 15 | |

```
Asp Leu Arg Pro Glu Ile Ala His Ala His Gln Pro Val Met Ser Pro
            20                  25                  30

Ser His His Gly Trp Asp Gly Asn Gly Ala Thr Ala Val Pro Thr Pro
        35                  40                  45

Met Pro Lys Arg Leu Asp Gly Lys Val Ala Ile Val Thr Gly Gly Ala
    50                  55                  60

Arg Gly Ile Gly Glu Ala Ile Val Arg Leu Phe Ala Lys His Gly Ala
65                  70                  75                  80

Arg Val Val Ile Ala Asp Ile Asp Asp Ala Ala Gly Glu Ala Leu Ala
                85                  90                  95

Ser Ala Leu Gly Pro Gln Val Ser Phe Val Arg Cys Asp Val Ser Val
            100                 105                 110

Glu Asp Asp Val Arg Arg Ala Val Asp Trp Ala Leu Ser Arg His Gly
        115                 120                 125

Gly Arg Leu Asp Val Tyr Cys Asn Asn Ala Gly Val Leu Gly Arg Gln
    130                 135                 140

Thr Arg Ala Ala Arg Ser Ile Leu Ser Phe Asp Ala Ala Glu Phe Asp
145                 150                 155                 160

Arg Val Leu Arg Val Asn Ala Leu Gly Ala Ala Leu Gly Met Lys His
                165                 170                 175

Ala Ala Arg Ala Met Ala Pro Arg Arg Ala Gly Ser Ile Val Ser Val
            180                 185                 190

Ala Ser Val Ala Ala Val Leu Gly Gly Leu Gly Pro His Ala Tyr Thr
        195                 200                 205

Ala Ser Lys His Ala Ile Val Gly Leu Thr Lys Asn Ala Ala Cys Glu
    210                 215                 220

Leu Arg Ala His Gly Val Arg Val Asn Cys Val Ser Pro Phe Gly Val
225                 230                 235                 240

Ala Thr Pro Met Leu Ile Asn Ala Trp Arg Gln Gly His Asp Asp Ala
                245                 250                 255

Thr Ala Asp Ala Asp Arg Asp Leu Asp Leu Asp Leu Asp Val Thr Val
            260                 265                 270

Pro Ser Asp Gln Glu Val Glu Lys Met Glu Glu Val Val Arg Gly Leu
        275                 280                 285

Ala Thr Leu Lys Gly Pro Thr Leu Arg Pro Arg Asp Ile Ala Glu Ala
    290                 295                 300

Val Leu Phe Leu Ala Ser Asp Glu Ala Arg Tyr Ile Ser Gly His Asn
305                 310                 315                 320

Leu Val Val Asp Gly Gly Val Thr Thr Ser Arg Asn Leu Ile Gly Leu
                325                 330                 335

Leu
```

(2) INFORMATION FOR SEQ ID NO:4:

(i) SEQUENCE CHARACTERISTICS:
        (A) LENGTH: 333 amino acids
        (B) TYPE: amino acid
        (C) STRANDEDNESS: single
        (D) TOPOLOGY: linear (xi) SEQUENCE DESCRIPTION: SEQ ID NO:4:

```
Met His Thr Thr Leu Ala Ser Tyr Ala Gln Asp Leu Ala Met Pro Ala
1               5                   10                  15

Ala Ala Leu Asp Leu Leu Pro Asp Lys Ala His Gln Pro Ser Met Ala
            20                  25                  30
```

|     |     |     |     |     |     |     |     |     |     |     |     |     |     |
|---|---|---|---|---|---|---|---|---|---|---|---|---|---|
| Pro | Ser | Leu<br>35 | His | Ala | Trp | Asp | Ser<br>40 | Pro | Asn | Gly | Ala | Pro<br>45 | Thr | Pro | Met |
| Pro | Lys<br>50 | Arg | Leu | Glu | Gly | Lys<br>55 | Val | Ala | Ile | Val | Thr<br>60 | Gly | Gly | Ala | Arg |
| Gly<br>65 | Ile | Gly | Glu | Ala | Ile<br>70 | Val | Arg | Leu | Phe | Val<br>75 | Lys | His | Gly | Ala | Lys<br>80 |
| Val | Val | Ile | Ala | Asp<br>85 | Ile | Asp | Ala | Ala | Gly<br>90 | Glu | Ala | Leu | Ala<br>95 | Ala |
| Ala | Leu | Gly | Pro<br>100 | His | Val | Gly | Phe | Val<br>105 | Arg | Cys | Asp | Val<br>110 | Ser | Val | Glu |
| Glu | Asp | Val<br>115 | Glu | Arg | Ala | Val | Glu<br>120 | Arg | Ala | Val | Ala | Arg<br>125 | Tyr | Gly | Arg |
| Leu | Asp<br>130 | Val | Leu | Cys | Asn | Asn<br>135 | Ala | Gly | Val | Leu | Gly<br>140 | Arg | Gln | Thr | Arg |
| Ala | Ala<br>145 | Lys | Ser | Ile | Leu<br>150 | Ser | Phe | Asp | Ala | Gly<br>155 | Glu | Phe | Asp | Arg | Val<br>160 |
| Leu | Arg | Val | Asn | Ala<br>165 | Leu | Gly | Ala | Ala | Leu<br>170 | Gly | Met | Lys | His | Ala<br>175 | Ala |
| Leu | Ala | Met | Thr<br>180 | Gln | Arg | Arg | Ala | Gly<br>185 | Ser | Ile | Ile | Ser | Val<br>190 | Ala | Ser |
| Val | Ala | Gly<br>195 | Val | Leu | Gly | Gly | Leu<br>200 | Gly | Pro | His | Ala | Tyr<br>205 | Thr | Ala | Ser |
| Lys | His<br>210 | Ala | Ile | Val | Gly | Leu<br>215 | Thr | Lys | Asn | Ala | Ala<br>220 | Cys | Glu | Leu | Gly |
| Ala<br>225 | His | Gly | Ile | Arg | Val<br>230 | Asn | Cys | Ile | Ser | Pro<br>235 | Phe | Gly | Val | Ala | Thr<br>240 |
| Pro | Met | Leu | Ile | Asn<br>245 | Ala | Trp | Arg | Gln | Gly<br>250 | His | Asp | Ala | Ser | Thr<br>255 | Ala |
| Asp | Asp | Ala | Asp<br>260 | Ala | Asp | Ile | Asp | Leu<br>265 | Asp | Ile | Ala | Val | Pro<br>270 | Ser | Asp |
| Gln | Glu | Val<br>275 | Glu | Lys | Met | Glu | Glu<br>280 | Val | Val | Arg | Gly | Leu<br>285 | Ala | Thr | Leu |
| Lys | Gly<br>290 | Ala | Thr | Leu | Arg | Pro<br>295 | Arg | Asp | Ile | Ala | Glu<br>300 | Ala | Ala | Leu | Phe |
| Leu | Ala<br>305 | Ser | Asp | Asp | Ser<br>310 | Arg | Tyr | Ile | Ser | Gly<br>315 | His | Asn | Leu | Val | Val<br>320 |
| Asp | Gly | Gly | Val | Thr<br>325 | Thr | Ser | Arg | Asn | Leu<br>330 | Ile | Gly | Leu |

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GTGGTCAGGG GCCT        14

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GTGGTCAGGG GACGTCAGGG GCCT                               24

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GTGGTCAGGG TCAGGGGCCT                                    20

( 2 ) INFORMATION FOR SEQ ID NO:8:

( i ) SEQUENCE CHARACTERISTICS:
        ( A ) LENGTH: 359 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:8:

```
Met His Xaa Xaa Leu Ala Ser Tyr Ala Xaa Xaa Xaa Ala Met Pro Xaa
 1           5                  10                  15

Xaa Ala Leu Asp Leu Xaa Pro Xaa Xaa Xaa Xaa Ala His Gln Pro Xaa
             20              25                  30

Met Xaa Pro Ser Xaa His Xaa Trp Asp Xaa Xaa Xaa Xaa Xaa Xaa Xaa
         35              40                  45

Pro Thr Pro Met Pro Lys Arg Leu Xaa Gly Lys Val Ala Ile Val Thr
     50              55                  60

Gly Gly Ala Arg Gly Ile Gly Glu Ala Ile Val Arg Leu Phe Xaa Lys
 65              70                  75                  80

His Gly Ala Xaa Val Val Ile Ala Asp Ile Asp Asp Ala Ala Gly Glu
                 85                  90                  95

Ala Leu Ala Xaa Ala Leu Gly Pro Xaa Val Xaa Phe Val Arg Cys Asp
             100                 105                 110

Val Ser Val Glu Xaa Asp Val Xaa Arg Ala Val Xaa Xaa Ala Xaa Xaa
             115                 120                 125

Arg Xaa Xaa Gly Arg Leu Asp Val Xaa Cys Asn Asn Ala Gly Val Leu
         130                 135                 140

Gly Arg Gln Thr Arg Ala Ala Xaa Ser Ile Leu Ser Phe Asp Ala Xaa
145                 150                 155                 160

Glu Phe Asp Arg Val Leu Arg Val Asn Ala Leu Gly Ala Ala Leu Gly
                 165                 170                 175

Met Lys His Ala Ala Xaa Ala Met Xaa Xaa Arg Arg Ala Gly Ser Ile
             180                 185                 190

Xaa Ser Val Ala Ser Val Ala Xaa Val Leu Gly Gly Leu Gly Pro His
         195                 200                 205

Ala Tyr Thr Ala Ser Lys His Ala Ile Val Gly Leu Thr Lys Asn Ala
     210                 215                 220

Ala Cys Glu Leu Xaa His Gly Xaa Arg Val Asn Cys Xaa Ser Pro Phe
225                 230                 235                 240

Gly Val Ala Thr Pro Met Leu Ile Asn Ala Trp Arg Gln Gly His Asp
             245                 250                 255

Xaa Xaa Thr Ala Asp Xaa Asp Xaa Asp Xaa Asp Xaa Asp Leu Asp Xaa
         260                 265                 270
```

-continued

```
        Xaa  Val  Pro  Ser  Asp  Gln  Glu  Val  Glu  Lys  Met  Glu  Glu  Val  Val  Arg
             275                      280                      285

Gly  Leu  Ala  Thr  Leu  Lys  Gly  Xaa  Thr  Leu  Arg  Pro  Arg  Asp  Ile  Ala
             290                 295                      300

Glu  Ala  Xaa  Leu  Phe  Leu  Ala  Ser  Asp  Xaa  Xaa  Arg  Tyr  Ile  Ser  Gly
        305                      310                 315                           320

His  Asn  Leu  Val  Val  Asp  Gly  Gly  Val  Thr  Thr  Ser  Arg  Asn  Leu  Ile
                            325                      330                      335

Gly  Leu  Xaa  Cys  Asn  Ser  Glu  Asn  Ser  Ser  Ser  Glu  Gln  Glu  Asn  Cys
                  340                      345                      350

Glu  Ser  Asp  Cys  Val  Pro  Met
                  355
```

( 2 ) INFORMATION FOR SEQ ID NO:9:

( i ) SEQUENCE CHARACTERISTICS:
    ( A ) LENGTH: 1288 base pairs
    ( B ) TYPE: nucleic acid
    ( C ) STRANDEDNESS: both
    ( D ) TOPOLOGY: linear ( i i ) MOLECULE TYPE: cDNA ( x i ) SEQUENCE DESCRIPTION: SEQ ID NO:9:

```
GACGCACTCG CCTCTTGTGT CTTTCTTTGT GAGCTGTGGT GTGGTGGTCG AGACACACAC      60

AGCAGCAGCA ACWASRACAG GKWCRTACAT GCACRCTASC CTCGCCTCCT ACGCCSMGGA     120

TCYMGCYATG CCTGSCGCYG SACCTCS-
RCC  YCSWSMYWGM SMASGCGCAC CAGCCSKYCA             180

TGKCGCCSTC KCWCCACGSC TGGGACGGCA ATGSCSCCAM WGSCGYSCCC ACWCCSATGC     240

CCAAGAGGCT GGAMGGGAAG GTGGCCATTG TSACSGGCGG SGCGMGSGGG ATCGGSGAGG     300

CSATCGTGMG GCTGTTCGYY AAGCACGGGG CCMRGGTGGT GATCGCGGAC ATCGACGACG     360

CSGCGGGSGA GGCGCTGGCG KCGGCGCTGG GSCCGCASGT CRGSTTCGTG CGSTGCGACG     420

TGTCSGTGGA GGASGACGTS SRGCGCGCCG TSGACTGSGC GCYGTSGCGC SRYGRCGGSC     480

GSCTSGACGT SYWSTGCAAC AACGCCGGGG TGCTGGGCCG CCAGACGCGC GCGGCCARGA     540

GCATCCTGTC STTCGACGCS GSSGAGTTCG ACCGCGTGCT CCGCGTCAAC GCGCTGGGCG     600

CCGCGCTCGG SATGAAGCAC GCGGCGCKCG CCATGACCCA GCGCCGCGCC GCGCGGGGAG     660

CATCRTCTCC GTCGCCAGCG TCGCSGSCGT GCTSGGCGGC CTCGGCCCGC ACGCCTACAC     720

CGCCTCCAAG CACGCCATCG TSGGGCTCAC CAAGAACGCC GCCTGCGAGC TSSGCGCSCA     780

CGGSRTCCGS GTCAACTGCR TCTCSCCCTT CGGCGTCGCC ACSCCSATGC TCATCAACGC     840

CTGGCGCCAG GGCCACGACG MCKCCACCGC CGACGMCGAC CGAGACSYCG ACMTCGACCT     900

CGACRTCRCC GTGCCCAGCG ACCAGGAGGT GGAGAAGATG GAGGAGGTGG TCAGGGGCCT     960

SGCCACGCTC AAGGGCSCSA CGCTSAGRCC CAGGGACATC GCCGAGGCGG YGCTCTTCCT    1020

SGCCAGCGAC GASKCCAGRT AYATWTCSGG CCACAACCTY GTCGTSGACG GCGGCGTCAC    1080

CACMTCCAGR AACCTMATYG GCYTKT-
GAMT  CWWYKTCAAT CCGYTCYARA TGAATSCSAT           1140

WSYYATRGCT ARSMYAAYTA GARAAG-
GATK  WGWKARWRWR MYGCWAYGYA RKTGTACTYG          1200

AAGYGATYSA TTYYCATTTK GTTRATYK-
MT  TSATYMAAWR WRWWAAWWRR ACTTGTGCAA            1260

CTGAGCATTG GCCCCCAAAA AAAAAAAA                                      1288
```